United States Patent [19]
Seth

[11] Patent Number: 6,143,327
[45] Date of Patent: Nov. 7, 2000

[54] DELAYED RELEASE COATED TABLET OF BUPROPION HYDROCHLORIDE

[75] Inventor: Pawan Seth, Irvine, Calif.

[73] Assignee: Pharma Pass LLC, Irvine, Calif.

[21] Appl. No.: 09/459,459

[22] Filed: Dec. 13, 1999

Related U.S. Application Data

[63] Continuation of application No. 09/184,091, Oct. 30, 1998.

[51] Int. Cl.$^7$ ............... A61K 9/32; A61K 9/36; A61K 9/22; A61K 31/135
[52] U.S. Cl. .......... 424/482; 424/468; 424/480
[58] Field of Search .................... 424/468, 480, 424/482; 514/646

[56] References Cited

U.S. PATENT DOCUMENTS

| | | |
|---|---|---|
| 4,687,660 | 8/1987 | Baker et al. . |
| 4,716,041 | 12/1987 | Kjornaes et al. . |
| 4,769,027 | 9/1988 | Baker et al. . |
| 5,427,798 | 6/1995 | Ludwig et al. . |
| 5,681,584 | 10/1997 | Savastano et al. . |

*Primary Examiner*—Thurman K. Page
*Assistant Examiner*—Alysia Berman
*Attorney, Agent, or Firm*—Alston & Bird LLP

[57] ABSTRACT

The invention provides a delayed release coated tablet, free of stabilizer and free of pore-forming agent comprising: (i) a core consisting essentially of bupropion hydrochloride, a binder and a lubricant; and (ii) a first coating consisting essentially of a water-insoluble, water-permeable film-forming polymer, a plasticizer and a water-soluble polymer; and (iii) a second coating consisting essentially of a methacrylic polymer and a plasticizer therefor.

19 Claims, No Drawings

DELAYED RELEASE COATED TABLET OF BUPROPION HYDROCHLORIDE

This application is a continuation of application Ser. No. 09/184,091, filed Oct. 30, 1998, now allowed.

BACKGROUND OF THE INVENTION

Bupropion (its salt hydrochloride) is a widely used antidepressant drug. A commercial example is Wellbutrin®. This product consists in immediate release tablet, 75 or 100 mg strength. However it has been proven that bupropion hydrochloride can induce some severe side effects. For example, seizures can occur in about 0.4% patients and this effect has been proven to be related with immediate release tablets because of the peak in bupropion plasmatic concentration induced by such a dosage form. The development of a new sustained release dosage form has therefore been considered as an appropriate means to overcome this situation.

U.S. Pat. No. 5,358,970 and U.S. Pat. No. 5,427,798, both to Burroughs Wellcome, describe a sustained release formulation of bupropion hydrochloride based on matrix technology. The term matrix refers to a tablet where the drug is embedded in an excipient that makes a non-disintegrating core called matrix. Drug diffusion occurs through this core. As bupropion hydrochloride is unstable, the product described in the above two patents requires a stabilizer to achieve sufficient stability. This stabilizer is an acidic compound, preferably cysteine hydrochloride. Matrix technology is however not suited for the manufacture of a tablet, since it implies the use of a stabilizer.

U.S. Pat. No. 4,687,660 and EP-A-0171457 disclose a tablet formed of a core and a coating, where the core comprises bupropion hydrochloride together with excipient(s) and optionally an osmotic enhancing agent and where the coating comprises a water-insoluble, water-permeable film-forming polymer (such as cellulose acetate), a pore-forming agent (such as impalpable lactose and sodium carbonate), and optionally a so-called water-permeability enhancing agent (such as polyethyleneglycol) and again optionally a plasticizer. This type of coating, since it requires pore-forming agent, cannot provide a uniform coating and therefore the release rate cannot be uniform from one tablet to another.

The prior art thus cannot afford tablets of bupropion hydrochloride without recourse to the matrix technology (and to a stabilizer) or without recourse to pore-forming agent in the coating.

SUMMARY OF THE INVENTION

The invention provides a delayed release coated tablet comprising:
(i) a core comprising bupropion hydrochloride and conventional excipients, free of stabilizer; and
(ii) a first coating consisting essentially of a water-insoluble, water-permeable film-forming polymer, a plasticizer and a water-soluble polymer,
(iii) a second coating consisting essentially of a methacrylic polymer and a plasticizer therefor.

The invention thus provides a new bupropion hydrochloride delayed release composition under the form of a coated tablet free of stabilizer of any kind including those with acidic pH or with antioxidant properties. Also, the delayed release is obtained thanks to a semi-permeable release coating, free of (monomeric) pore-forming agent.

The tablets of the invention exhibit specific dissolution profiles.

The invention also provides a tablet comprising the delayed release coated tablet of the invention, coated with a bupropion hydrochloride immediate release coating.

DETAILED DESCRIPTION OF THE INVENTION

The invention consists in a tablet comprising a core and a first coating and a second coating.

Core.

The core includes bupropion hydrochloride, and conventional excipients, notably a lubricant, and a binder and/or a filler, and optionally a glidant as well as other excipients.

Examples of lubricants include stearic acid, magnesium stearate, glyceryl behenate, talc, mineral oil (in PEG), etc. Glyceryl behenate is one preferred lubricant. Examples of binders include water-soluble polymer, such as modified starch, gelatin, polyvinylpyrrolidone, polyvinyl alcohol, etc. The preferred binder is polyvinyl alcohol. Examples of fillers include lactose, microcristalline cellulose, etc. An example of glidant is silicon dioxide (Aerosil® of Degussa). The above binders, lubricants, fillers, glidants, and any other excipient that may be present can further be found in the relevant literature, for example in the Handbook of Pharmaceutical Excipients. The relative amounts of ingredients in the core are preferably as follows. The proportion of bupropion hydrochloride in the core may vary between 70 and 98% of the core dry weight. The proportion of lubricant in the core may vary between 0.5 and 10% of the core dry weight. The proportion of binder or filler in the core may vary between 2 and 25% of the core dry weight.

The manufacturing process of the core can be as follows. Bupropion hydrochloride is first granulated with a binder, in a granulator, preferably but not necessarily a fluidized bed granulator. The binder is first dissolved or dispersed in a suitable solvent, preferably water. The solution or suspension of binder is then sprayed onto the drug in a granulator, e.g. fluidized bed granulator. For example, fluidized bed granulators manufactured by Glatt (Germany) or Aeromatic (Switzerland) can be used for this operation. An alternative process can be to use a conventional or high shear mixer to proceed granulation. If necessary, the drug can be mixed with a filler, prior to the granulation step. Granules once dried can be mixed with the other excipients, especially with the lubricant, but also with glidants and any other excipient suitable to improve processing. The mixture of granules (preferably with lubricant), and optionally glidant is pressed into tablets. Alternatively, the active ingredient and lubricant can be mixed in a granulator, e.g. a fluidized bed granulator, and heated to the melting point of the lubricant to form granules. This mixture can then be mixed with a suitable filler and compressed into tablets. Also, it is possible to mix the active ingredient and the lubricant (e.g. mineral oil in PEG) in a granulator, e.g. a fluidized bed granulator, and then to press the resulting granules into tablets. Tablets can be obtained by standard techniques, e.g. on a (rotary) press (for example Manesty Betapress®) fitted with suitable punches. The resulting tablets are hereinafter referred as tablet cores.

First coating.

These tablet cores are then coated with the first coating, i.e. the semi-permeable coating designed to achieve a delayed release of bupropion hydrochloride.

The first coating comprises a water-insoluble, water-permeable film-forming polymer, together with a plasticizer and a water-soluble polymer.

The water-insoluble, water-permeable film-forming polymer can be a cellulose ether, such as ethylcellulose, a cellulose ester, such as cellulose acetate, polyvinylalcohol, etc. The preferred film-forming polymer is ethylcellulose (available from Dow Chemical under the trade name Ethocel®). The plasticizer can be an ester such as a citrate ester, an oil such as castor oil, a polyalkyleneglycol such as polyethyleneglycol of various MWs. The preferred plasticizer is polyethyleneglycol. The water-soluble polymer is preferably polyvinylpyrrolidone. Some other excipients can be used in the coating, as for example acrylic acid derivatives (available from Roehm Pharma under the trade name "Eudragit®"), pigments, etc. The relative amounts of ingredients in the coating are preferably as follows. The proportion of water-insoluble, water-permeable polymer (e.g. ethylcellulose) in the coating may vary between 20 and 85% of the coating dry weight. The proportion of water-soluble polymer (e.g. polyvinylpyrrolidone) in the coating may vary between 10 and 75% of the coating dry weight. The proportion of plasticizer (e.g. polyethyleneglycol) in the coating may vary between 5 and 30% of the coating dry weight. The relative proportions of ingredients, notably the ratio water-insoluble, water-permeable film-forming polymer to water-soluble polymer, can be varied depending on the release profile to be obtained (where a more delayed release is generally obtained with a higher amount of water-insoluble, water-permeable film-forming polymer).

The coating process can be as follows. Ethylcellulose and polyethylene glycol (e.g. PEG 1450) are dissolved in a solvent such as ethanol; polyvinylpyrrolidone is then added. The resulting solution is sprayed onto the tablet cores, using a coating pan or a fluidized bed apparatus.

The weight ratio coating/tablet core is comprised e.g. between 1/30 and 3/10, preferably about 1/10.

Second coating.

These coated tablet cores are then coated with the second coating, which is aimed at protecting the component from coming into contact with the gastric juice and to avoid the food effect.

The second coating comprises an enteric polymer of the methacrylic type and a plasticizer.

The enteric polymer, notably of the methacrylic type can be for example methacrylic acid co-polymer type C, and is available under the tradename Eudragit (e.g. of the grade L30D-55). The plasticizer can be an ester such as a citrate ester, notably triethyl citrate, a polyalkyleneglycol such as polyethyleneglycol of various MWs. The preferred plasticizer is a mixture of triethyl citrate and polyethyleneglycol. Other conventional additives as disclosed above are also possible, notably silicon dioxide. The relative amounts of ingredients in the coating are preferably as follows. The proportion of enteric polymer (e.g. Eudragit L30D-55) may vary between 40 and 90% of the coating dry weight. The proportion of plasticizer (e.g. triethyl citrate, polyethyleneglycol) in the coating may vary between 10 and 60% of the coating dry weight. The relative proportions of ingredients, notably the ratio methacrylic polymer to plasticizer can be varied according to a practice known to the skilled man.

The coating process can be as follows. Triethyl citrate and polyethylene glycol (e.g. PEG 1450) are dissolved in a solvent such as water; methacrylic polymer is then added. If present, silicon dioxide can be added as a suspension. The resulting solution is sprayed onto the coated tablet cores, using a coating pan or a fluidized bed apparatus.

The weight ratio coating/coated tablet core is comprised e.g. between 1/30 and 3/10, preferably about 1/10.

The tablet comprises an amount of bupropion hydrochloride that can be from 50 to 400 mg per tablet.

Surprisingly, it was discovered that the above formulation did not lead to any degradation of bupropion hydrochloride though no stabilizer was present in the formulation. Stability studies were conducted in oven, under the storage test conditions described in the US pharmacopoeia $23^{rd}$ edition page 1961. Under these conditions no significant change in drug potency could be seen.

Surprisingly, it was also discovered that the above formulation did provide a delayed (sustained) release though no pore-forming agent was present in the coating.

The invention thus provides a bupropion hydrochloride delayed release coated tablet free of stabilizer and free of pore-forming agent, exhibiting a dissolution profile such that after 2 hours, from 0 up to 30% of the bupropion hydrochloride is released, after 4 hours, from 3 to 22% of the bupropion hydrochloride is released, after 6 hours, from 15 to 38% of the bupropion hydrochloride is released, after 8 hours, more than 40% of the bupropion hydrochloride is released.

Best modes for carrying the invention.

A preferred tablet composition comprises:

(i) a core consisting essentially of bupropion hydrochloride, polyvinylalcohol and glyceryl behenate; and
(ii) a first coating consisting essentially of ethylcellulose, polyvinylpyrrolidone and polyethyleneglycol, and
(iii) a second coating consisting essentially of methacrylic acid co-polymer type C, triethyl citrate, polyethyleneglycol and optionally silicon dioxide.

EXAMPLES

The following examples illustrate the invention without limiting it, where the amounts are given per dosage form.

Example 1

The following formulation is prepared.

| Ingredients | Amount (mg) |
| --- | --- |
| Bupropion hydrochloride | 150.00 |
| Kollidon 90F (povidone USP) | 9.00 |
| Purified Water | 171.00 |

-continued

| Ingredients | Amount (mg) |
|---|---|
| Stearic Acid | 3.20 |
| Total (dry weight) | 162.20 |

Povidone is first dissolved in water. Bupropion hydrochloride is placed in the top spraying chamber of Glatt GPCG1 fluidized bed apparatus. The solution of povidone is sprayed onto the active ingredient, with the following parameters:

| | |
|---|---|
| Air flow (m³/h) | 100–110 m³/h |
| Liquid flow (g/min) | 6–7 g/min |
| Inlet temperature | 65° C. |
| Spraying pressure | 2.8 bar |

Once the granulation is completed, granules are passed through a sieve (1 mm mesh) and stearic acid is weighed, added and blended in a drum mixer (Turbula T2C, Bachoffen, Switzerland). The resulting mixture is pressed into tablets (7 mm diameter and 7 mm curvature) with average hardness being between 60 and 120N. These tablet cores are then coated with the following formulation.

| Ingredients | Amount (mg) |
|---|---|
| Tablet cores | 162.20 |
| Ethocel PR100 (ethylcellulose) | 7.05 |
| Kollidon 90F (povidone USP) | 7.05 |
| PEG 1450 | 2.10 |
| Denatured alcohol | 210.00 |
| Total (dry weight) | 178.40 |

Ethocel, povidone and PEG 1450 are first dissolved in denatured alcohol. The coating solution is then sprayed onto the tablet cores in a coating pan (Vector LCDS), with the following spraying parameters:

| | |
|---|---|
| Air flow (m³/h) | 100–110 m³/h |
| Liquid flow (g/min) | 6–7 g/min |
| Inlet temperature | 65° C. |
| Spraying pressure | 2.8 bar |

Stability data

Storage conditions: conforms to USP 23 guideline (25° C. and 60% relative humidity and 40° C. and 75% relative humidity). Assay: HPLC method.

| | Bupropion hydrochloride content (%) | | | |
|---|---|---|---|---|
| Storage conditions | 0 day | 30 days | 60 days | 90 days |
| 25° C./60% RH | 100.4 | — | — | 99.6 |
| 40° C./75% RH | 100.4 | 98.9 | 99.2 | 99.1 |

Dissolution profile
  Dissolution conditions:
  Medium: 1000 ml 0.1N HCl.
  Method: 75 rpm USP Apparatus I.

| Time (hour) | Release rate (%) |
|---|---|
| 0 | 0 |
| 1 | 37 |
| 2 | 62 |
| 3 | 80 |
| 4 | 92 |

Example 2 modified coating

Tablet cores are prepared as stated is example 1. However, to allow a good identification of the tablets the coating was modified by addition of 0.60 mg of a iron oxide red pigment, leading to a final total weight of 179 mg. The coating and coating process are as in example 1. The dissolution profile is identical to the one disclosed in example 1.

Example 3

The procedure of example 1 was repeated except that tablets with 100 mg potency were prepared:

| Ingredients | Amount (mg) |
|---|---|
| Bupropion hydrochloride | 100.00 |
| Kollidon 90F (povidone USP) | 6.00 |
| Purified Water | 140.00 |
| Stearic Acid | 2.20 |
| Total (dry weight) | 108.20 |

The process was not modified except that tablets were pressed in 6 mm diameter and 6 mm curvature radius. Tablets were then coated with the following formulation:

| Ingredients | Amount (mg) |
|---|---|
| Tablet cores | 108.20 |
| Ethocel PR100 (ethylcellulose) | 5.00 |
| Kollidon 90F (povidone USP) | 5.00 |
| PEG 1450 | 1.50 |
| Denatured alcohol | 150.00 |
| Total (dry weight) | 119.70 |

The coating process is as in example 1.

The dissolution profile is similar to the one disclosed in example 1.

Example 4

The procedure of example 1 was repeated except that tablets with 200 mg potency were prepared:

| Ingredients | Amount (mg) |
|---|---|
| Bupropion hydrochloride | 100.00 |
| Kollidon 90F (povidone USP) | 12.00 |
| Purified Water | 280.00 |

-continued

| Ingredients | Amount (mg) |
|---|---|
| Stearic Acid | 4.40 |
| Total (dry weight) | 216.40 |

The process was not modified except that tablets were pressed in 8 mm diameter and 8 mm curvature radius. Tablets were then coated with the following formulation:

| Ingredients | Amount (mg) |
|---|---|
| Tablet cores | 216.40 |
| Ethocel PR100 (ethylcellulose) | 9.00 |
| Kollidon 90F (povidone USP) | 9.00 |
| PEG 1450 | 2.80 |
| Denatured alcohol | 240.00 |
| Total (dry weight) | 237.20 |

The coating process is as in example 1.

The dissolution profile is similar to the one disclosed in example 1.

Example 5
immediate release+controlled release system

In this formulation, one part of bupropion hydrochloride mixed with a binder is sprayed onto the coated tablet of example 1. This allows an immediate release of the external active whereas the internal part is released under controlled conditions.

The following formulation is prepared:

| Ingredients | Amount (mg) |
|---|---|
| Bupropion hydrochloride | 135.00 |
| Kollidon 90F (povidone USP) | 9.00 |
| Purified Water | 160.00 |
| Stearic Acid | 3.20 |
| Total (dry weight) | 147.20 |

The preparation process is identical to the one of example 1. These tablet cores are then coated with the following formulation.

| Ingredients | Amount (mg) |
|---|---|
| Tablet cores | 147.20 |
| Ethocel PR100 (ethylcellulose) | 7.05 |
| Kollidon 90F (povidone USP) | 7.05 |
| PEG 1450 | 2.10 |
| Denatured alcohol | 210.00 |
| Total (dry weight) | 163.40 |

The coating process is as in example 1. A second coating containing the remaining of the active is then sprayed. Formulation is as follows:

| Ingredients | Amount (mg) |
|---|---|
| Tablet | 163.40 |
| Bupropion hydrochloride | 15.00 |

-continued

| Ingredients | Amount (mg) |
|---|---|
| Ethocel PR100 (ethylcellulose) | 5.00 |
| Denatured alcohol | 30.00 |
| Total (dry weight) | 183.40 |

The coating process is furthered in a manner identical to the one of example 1.

The dissolution profile is the result of the combination of two profiles, where the first one is an immediate release profile and the second one corresponds substantially to the one disclosed in example 1.

Example 6

The following formulation is prepared.

| Ingredients | Amount (mg) |
|---|---|
| Bupropion hydrochloride | 150.00 |
| Stearic Acid | 5.00 |
| Avicel (microcrist. cellulose) | 20.00 |
| No solvent required | — |
| Total (dry weight) | 185.00 |

Bupropion hydrochloride and stearic acid are placed in the chamber of Glatt GPCG1 fluidized bed apparatus. The powders are fluidized with hot air. The powders are heated until the product temperature reaches 50–55° C.; at this point granulation takes place. The product is then cooled to room temperature.

| | |
|---|---|
| Air flow (m$^3$/h) | 100–110 m$^3$/h |
| Inlet temperature | 60–65° C. |

Once the granulation is completed, granules are passed through a sieve (1 mm) and microcristalline cellulose is weighted, added and blended in a drum mixer (Turbula T2C, Bachoffen, Switzerland). The resulting mixture is pressed into tablets (7 mm diameter and 7 mm curvature) with average hardness being between 50 and 120N. These tablet cores are then coated with the following formulation.

| Ingredients | Amount (mg) |
|---|---|
| Tablet cores | 172.00 |
| Ethocel PR100 (ethylcellulose) | 5.00 |
| Kollidon 90F (povidone USP) | 5.00 |
| PEG 1450 | 1.50 |
| Denatured alcohol | 210.00 |
| Total (dry weight) | 183.50 |

The coating process is as in example 1.

The dissolution profile is similar to the one disclosed in example 1.

Example 7

Example 6 is reproduced, except that the following coating is used.

| Ingredients | Amount (mg) |
| --- | --- |
| Tablet cores | 172.00 |
| Ethocel PR100 (ethylcellulose) | 8.00 |
| Kollidon 90F (povidone USP) | 3.00 |
| PEG 1450 | 2.00 |
| Denatured alcohol | 300.00 |
| Total (dry weight) | 190.00 |

Dissolution profile

Dissolution conditions: identical to example 1.

| Time (hour) | Release rate (%) |
| --- | --- |
| 0 | 0 |
| 1 | 7 |
| 4 | 38 |
| 6 | 58 |
| 8 | 75 |

Examples 8 and 9

Examples 6 and 7 are reproduced, except that the following core formulation is used.

| Ingredients | Amount (mg) |
| --- | --- |
| Bupropion hydrochloride | 150.00 |
| Glyceryl behenate | 10.00 |
| Avicel (microcrist. Cellulose) | 20.00 |
| No solvent required | — |
| Total (dry weight) | 190.00 |

The manufacturing process is identical to the one of examples 6 and 7, except that the powder mixture is heated to 65° C.

The dissolution profiles are similar to the ones disclosed in examples 1 and 7, respectively.

Example 10

The following core composition is used.

| Ingredients | Amount (mg) |
| --- | --- |
| Bupropion hydrochloride | 150.00 |
| Polyethylene Glycol 8000 | 22.50 |
| Mineral oil | 3.00 |
| Purified Water | 120.00 |
| Total (dry weight) | 175.50 |

Polyethylene glycol 8000 is first dissolved in water. Mineral oil is then suspended in the PEG solution. Bupropion hydrochloride is placed in the top spraying chamber of Glatt GPCG1 fluidized bed apparatus. The solution of PEG and mineral oil is sprayed onto the active ingredient, with the following parameters:

| | |
| --- | --- |
| Air flow (m³/h) | 100–110 m³/h |
| Liquid flow (g/min) | 6–7 g/min |
| Inlet temperature | 65° C. |
| Spraying pressure | 2.2 bar |

Once the granulation is completed, granules are passed through a sieve (1 mm mesh) and pressed into tablets (7 mm diameter and 7 mm curvature) with average hardness being between 50 and 120N. These tablet cores are then coated with the following formulation.

| Ingredients | Amount (mg) |
| --- | --- |
| Tablet cores | 175.50 |
| Ethocel PR100 (ethylcellulose) | 5.00 |
| Kollidon 90F (povidone USP) | 5.00 |
| PEG 1450 | 1.50 |
| Denatured alcohol | 210.00 |
| Total (dry weight) | 187.00 |

The coating process is as in example 1. The dissolution profile is similar to the one disclosed in example 1.

Example 11

Example 10 is reproduced, except that the following coating formulation is used.

| Ingredients | Amount (mg) |
| --- | --- |
| Tablet cores | 175.50 |
| Ethocel PR100 (ethylcellulose) | 8.00 |
| Kollidon 90F (povidone USP) | 3.00 |
| PEG 1450 | 2.00 |
| Denatured alcohol | 300.00 |
| Total (dry weight) | 188.50 |

The dissolution profile is similar to the one disclosed in example 7.

Example 12

The following formulation is prepared.

| Ingredients | Amount (mg) |
| --- | --- |
| Bupropion hydrochloride | 150.00 |
| PVA (Polyvinayl Acetate USP) | 5.30 |
| Purified Water | 110.00 |
| Glyceryl behenate | 4.70 |
| Total (dry weight) | 160.00 |

PVA is first dissolved in water. Bupropion hydrochloride is placed in the top spraying chamber of Glatt GPCG1 fluidized bed apparatus. The solution of PVA is sprayed onto the active ingredient, with the following parameters:

| | |
| --- | --- |
| Air flow (m³/h) | 100–110 m³/h |
| Liquid flow (g/min) | 6–7 g/min |
| Inlet temperature | 65° C. |
| Spraying pressure | 2.8 bar |

Once the granulation is completed, granules are passed through a sieve (1 mm mesh) and glyceryl behenate is weighed, added and blended in a drum mixer (Turbula T2C, Bachoffen, Switzerland). The resulting mixture is pressed into tablets (7 mm diameter and 7 mm curvature) with average hardness being between 60 and 120N. These tablet cores are then coated with the following formulation.

first coating

| Ingredients | Amount (mg) |
| --- | --- |
| Tablet cores | 160.00 |
| Ethocel PR100 (ethylcellulose) | 7.00 |
| Kollidon 90F (povidone USP) | 3.00 |
| PEG 1450 | 1.50 |
| Denatured alcohol | 210.00 |
| Total (dry weight) | 171.50 |

Ethocel, povidone and PEG 1450 are first dissolved in denatured alcohol. The coating solution is then sprayed onto the tablet cores in a coating pan (Vector LCDS), with the following spraying parameters:

| | |
| --- | --- |
| Air flow (m$^3$/h) | 100–110 m$^3$/h |
| Liquid flow (g/min) | 6–7 g/min |
| Inlet temperature | 65° C. |
| Spraying pressure | 2.8 bar | second coating

| Ingredients | Amount (mg) |
| --- | --- |
| Coated tablets | 171.50 |
| Eudragit L30 D-55 | 7.00 |
| Silicon dioxide | 2.10 |
| PEG 1450 | 1.40 |
| Triethyl citrate | 0.70 |
| Water | 40.00 |
| Total (dry weight) | 182.70 |

PEG and triethyl citrate 1450 are first dissolved in half the quantity of water. Eudragit is then added to the solution and stirred for 45 minutes. Silicon dioxide is suspended in the remaining quantity of water and is homogenized. The silicon dioxide suspension is then added to the Eudragit dispersion. The tablets are coated in a coating pan (Vector LCDS), with the following spraying parameters:

| | |
| --- | --- |
| Air flow (m$^3$/h) | 100–110 m$^3$/h |
| Liquid flow (g/min) | 6–7 g/min |
| Inlet temperature | 55° C. |
| Spraying pressure | 2.8 bar |

Dissolution profile

Dissolution conditions are the same as above, i.e. simulated gastric buffer with pH 1.5 at 37° C.

| Time (hour) | Release rate (%) |
| --- | --- |
| 2 | 0–8 |
| 4 | 5–22 |
| 6 | 15–38 |
| 8 | >40 |

The invention is not limited to the specific embodiments described above but can be varied within broad limits by the skilled man.

What is claimed is:

1. A delayed release coated tablet comprising:
   (i) a core comprising bupropion hydrochloride and conventional excipients, free of stabilizer; and
   (ii) a first coating consisting essentially of a water-insoluble, water-permeable film-forming polymer, a plasticizer and a water-soluble polymer; and
   (iii) a second coating consisting essentially of a methacrylic polymer and a plasticizer therefor;
   exhibiting a dissolution profile such that after 2 hours, from 0 up to 30% of the bupropion hydrochloride is released, after 4 hours, from 3 to 22% of the bupropion hydrochloride is released, after 6 hours, from 15 to 38% of the bupropion hydrochloride is released, after 8 hours, more than 40% of the bupropion hydrochloride is released.

2. The tablet of claim 1, where the water-insoluble, water-permeable film-forming polymer is ethylcellulose.

3. The tablet of claim 1, where the water-soluble polymer is polyvinylpyrrolidone.

4. The tablet of claim 1, where the plasticizer is polyethyleneglycol.

5. The tablet of claim 1, where the methacrylic polymer is a methacrylic acid co-polymer.

6. The tablet of claim 1, where the plasticizer for the methacrylic polymer is triethyl citrate, polyethyleneglycol or a mixture thereof.

7. The tablet of claim 1, where in the first coating, the water-insoluble, water-permeable film-forming polymer is ethylcellulose, the water-soluble polymer is polyvinylpyrrolidone, the plasticizer is polyethyleneglycol and where in the second coating, the methacrylic polymer is a methacrylic acid co-polymer, the plasticizer is triethyl citrate, polyethyleneglycol or a mixture thereof.

8. The tablet of claim 1, where the core comprises a binder and a lubricant.

9. The tablet of claim 8, where the core comprises polyvinyl alcohol and glyceryl behenate.

10. The tablet of claim 1, comprising from 50 to 400 mg bupropion hydrochloride.

11. The tablet of claim 7, comprising from 50 to 400 mg bupropion hydrochloride.

12. The tablet of claim 9, comprising from 50 to 400 mg bupropion hydrochloride.

13. A delayed release coated tablet comprising:
   (i) a core consisting essentially of bupropion hydrochloride, polyvinylalcohol and glyceryl behenate; and
   (ii) a first coating consisting essentially of ethylcellulose, polyvinylpyrrolidone and polyethyleneglycol; and
   (iii) a second coating consisting essentially of methacrylic acid co-polymer, triethyl citrate, polyethyleneglycol and optionally silicon dioxide;

exhibiting a dissolution profile such that after 2 hours, from 0 up to 30% of the bupropion hydrochloride is released, after 4 hours, from 3 to 22% of the bupropion hydrochloride is released, after 6 hours, from 15 to 38% of the bupropion hydrochloride is released, after 8 hours, more than 40% of the bupropion hydrochloride is released.

14. The tablet of claim 13, comprising from 50 to 400 mg bupropion hydrochloride.

15. A bupropion hydrochloride delayed release coated tablet free of stabilizer and free of pore-forming agent, exhibiting a dissolution profile such that after 2 hours, from 0 up to 30% of the bupropion hydrochloride is released, after 4 hours, from 3 to 22% of the bupropion hydrochloride is released, after 6 hours, from 15 to 38% of the bupropion hydrochloride is released, after 8 hours, more than 40% of the bupropion hydrochloride is released.

16. The tablet of claim 15, comprising from 50 to 400 mg bupropion hydrochloride.

17. A tablet comprising the delayed release coated tablet of claim 1, coated with a bupropion hydrochloride immediate release coating.

18. A tablet comprising the delayed release coated tablet of claim 13, coated with a bupropion hydrochloride immediate release coating.

19. A tablet comprising the delayed release coated tablet of claim 15, coated with a bupropion hydrochloride immediate release coating.

* * * * *